US012708392B2

(12) United States Patent
Mishima et al.

(10) Patent No.: US 12,708,392 B2
(45) Date of Patent: Aug. 18, 2026

(54) ASPIRATION SYSTEM AND ASPIRATION METHOD

(71) Applicant: TERUMO KABUSHIKI KAISHA, Tokyo (JP)

(72) Inventors: Yoshiki Mishima, Cupertino, CA (US); Kazuaki Kanamoto, Hadano city (JP); Masaomi Imai, Kofu-city (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 141 days.

(21) Appl. No.: 18/617,173

(22) Filed: Mar. 26, 2024

(65) Prior Publication Data

US 2024/0325037 A1 Oct. 3, 2024

(30) Foreign Application Priority Data

Mar. 27, 2023 (JP) ................................ 2023-050104

(51) Int. Cl.
*A61B 17/221* (2006.01)
*A61B 17/32* (2006.01)

(52) U.S. Cl.
CPC .... *A61B 17/221* (2013.01); *A61B 2017/2215* (2013.01); *A61B 2017/320064* (2013.01)

(58) Field of Classification Search
CPC . A61B 17/00234; A61B 17/22; A61B 17/221; A61B 17/3207; A61B 17/320758; A61B 2017/22079; A61B 2017/2215; A61B 2017/320004; A61B 2017/320024; A61B 2017/320028; A61B 2017/320032; A61B 2017/320064; A61B 2017/320716; A61B 2017/320741; A61B 2090/036
USPC .................................................. 606/159, 200
See application file for complete search history.

(56) References Cited

U.S. PATENT DOCUMENTS 8,435,228 B2 5/2013 Wulfman et al.
2019/0021758 A1* 1/2019 Nishio .......... A61B 17/320783

* cited by examiner

*Primary Examiner* — Kankindi Rwego
(74) *Attorney, Agent, or Firm* — Buchanan Ingersoll & Rooney PC

(57) ABSTRACT

An aspiration system is disclosed that is configured to capture and aspirate a thrombus flowing within a blood vessel and includes a capture device provided with an expandable capture unit and a capture wire extending from the capture unit, and an aspiration device provided with an aspiration tube and an aspiration port. The capture unit includes a plurality of linear members that is deformable and braided, a distal side coupler that couples distal portions of the plurality of linear members, and a proximal side coupler that couples proximal portions of the plurality of linear members and is coupled to the capture wire. The proximal side coupler includes an inner tube and an outer tube. The inner tube has a proximal portion located closer to the proximal side of the proximal side coupler than a proximal portion of the outer tube.

10 Claims, 8 Drawing Sheets

10
X
Y
320
162
173
161
172
160
221
171
220
212
170
235
236
237
232
230
233
234
231
400
200
211
210
602
604
600
601
211
216
215
111
110
150
130
131
100
140
320
340
500
318
317
310
314
311
300
330

ASPIRATION SYSTEM AND ASPIRATION METHOD

CROSS-REFERENCES TO RELATED APPLICATIONS

This application claims priority to Japanese Application No. 2023-050104 filed on Mar. 27, 2023, the entire content of which is incorporated herein by reference.

TECHNOLOGICAL FIELD

The present disclosure generally relates to an aspiration system and an aspiration method for capturing and aspirating an object flowing within a lumen of a living body.

BACKGROUND DISCUSSION

As a treatment for an intravenous thrombus, a catheter is percutaneously inserted into a vein to physically excise and remove the thrombus (see, for example, U.S. Pat. No. 8,435,228). In such a treatment, when the thrombus completely or partially avulsed from the wall of a blood vessel moves along with a blood flow and reaches the lung, a pulmonary embolism may occur. To avoid such a pulmonary embolism, in a known method, a device including an elongated wire that has a distal portion provided with a filter for capturing a thrombus is deployed in a blood vessel before thrombectomy. The thrombus captured by the filter is aspirated by an aspiration device and removed to the outside of the body.

U.S. Pat. No. 8,435,228 discloses couplers obtained by clamping and fixing a distal portion and a proximal portion of a plurality of braided wire rods that forms a filter between an inner tube and an outer tube of a double tube. In the coupler on the proximal side of the filter, a capture wire is clamped and fixed together with the linear members between the inner tube and the outer tube.

U.S. Pat. No. 8,435,228 also discloses relative reciprocating motion of the capture wire and an aspiration device for floating a thrombus accumulated in the filter. Furthermore, the coupler on the proximal side of the filter is reciprocated and put in and out of an opening of an aspiration catheter, and this reciprocating motion by the coupler deforms or breaks the thrombus and pushes the thrombus into the aspiration catheter, whereby the thrombus can be aspirated.

In U.S. Pat. No. 8,435,228, when the capture wire and the aspiration device are reciprocated relative to one another to put the coupler on the proximal side of the filter in and out of the opening of the aspiration device, the outer tube of the coupler on the proximal side of the filter is located on the outer side of the capture wire and easily comes into contact with the opening of the aspiration device. For this reason, the outer tube can get rather easily caught on the opening of the aspiration device, which may cause a difficulty in smoothly removing the thrombus or other objects.

SUMMARY

An aspiration system and an aspiration method are disclosed, which are capable of smoothly drawing an object captured by a capture unit into an aspiration device.

(1) An aspiration system according to the present disclosure that is capable of capturing and aspirating an object flowing within a lumen of a living body, the aspiration system including: a capture device provided with an expandable capture unit and a capture wire extending from the capture unit; and an aspiration device provided with a sheath having a distal end opening and an aspiration port communicating with an inner cavity of the sheath, wherein the capture unit includes a plurality of linear members that is deformable and braided into a net-like cylindrical body, a distal side coupler that couples distal portions of the plurality of linear members, and a proximal side coupler that couples proximal portions of the plurality of linear members and is coupled to the capture wire, the proximal side coupler includes an inner tube and an outer tube that surrounds the inner tube, and the inner tube has a proximal portion located closer to a proximal side of the proximal side coupler than a proximal portion of the outer tube.

In the aspiration system according to (1), the proximal portion of the inner tube enters through the distal end opening of the aspiration device before the proximal portion of the outer tube does, and subsequently, the proximal portion of the outer tube is guided by the inner tube and smoothly enters through the distal end opening. Accordingly, the proximal side coupler of the capture unit smoothly enters through the opening on the distal side of the sheath of the aspiration device. For this reason, this aspiration system enables the object captured by the capture unit to be drawn into the sheath more effectively by the proximal side coupler.

(2) In the aspiration system according to (1), the inner tube may have an inner tube bevel on the proximal side that is inclined at an angle of more than 0 degrees and less than 90 degrees relative to a longitudinal direction of the capture wire. Accordingly, when the proximal side coupler is drawn into the distal end opening of the sheath, the inner tube is smoothly drawn into the sheath with the inner tube bevel moving along the distal end opening of the sheath.

(3) In the aspiration system according to (1) or (2), the outer tube may have an outer tube bevel on the proximal side that is inclined at an angle of more than 0 degrees and less than 90 degrees relative to a longitudinal direction of the capture wire. Accordingly, when the proximal side coupler is drawn into the distal end opening of the sheath, the outer tube is smoothly drawn into the sheath with the outer tube bevel moving along the distal end opening of the sheath.

(4) In the aspiration system according to any one of (1) to (3), the inner tube and the outer tube each may have a most proximal end protruding toward the proximal side of the proximal side coupler that is covered with a resin material. Accordingly, when the proximal side coupler is drawn into the distal end opening of the sheath, it is possible to prevent the most proximal ends of the inner tube and the outer tube protruding toward the proximal side from damaging the sheath.

(5) In the aspiration system according to any one of (1) to (4), the linear members and the capture wire may be clamped and fixed between the inner tube and the outer tube. Accordingly, the linear members and the capture wire are clamped and firmly fixed between the outer tube and the inner tube.

(6) In the aspiration system according to any one of (1) to (5), the aspiration device may include an opening-closing unit as a stopcock that is connected to the aspiration port and capable of opening and closing a passage, the opening-closing unit may include an opening-closing operating portion movable in a linear opening-closing direction, the passage may be opened in an open state where the opening-closing operating portion is located at a first position, and the passage may be closed in a closed state where the opening-closing operating portion is located at a second position different from the first position. Accordingly, the aspiration system easily and reliably conducts starting and stopping operations for aspiration using the aspiration device, thereby enhancing the operability.

(7) An aspiration method according to the present disclosure includes a method for capturing and aspirating an object flowing within a lumen of a living body, the aspiration method involving: inserting an aspiration device into the lumen of the living body; inserting a capture device provided with a capture unit being expandable and a capture wire extending from the capture unit into an inner cavity of the aspiration device and moving the capture device to a desired position; inserting the capture wire through a lumen of an excision device and inserting the excision device into an inner cavity of the aspiration device and moving the excision device to a desired position; excising a lesion with the excision device; withdrawing the excision device from the aspiration device; allowing the aspiration device to start aspiration of the object, or the excised lesion, captured by the capture unit; and allowing the capture wire and the aspiration device to move relatively in a distal direction and a proximal direction at a frequency of 2 times/second to 5 times/second. Accordingly, in the aspiration method, since the object captured by the capture unit effectively floats away from the capture unit, the object captured by the capture unit is effectively aspirated by the aspiration device.

(8) An aspiration method according to the present disclosure includes a method for capturing and aspirating an object flowing within a lumen of a living body, the aspiration method involving: inserting an aspiration device into the lumen of the living body; inserting a capture device provided with a capture unit being expandable and a capture wire extending from the capture unit into an inner cavity of the aspiration device and moving the capture device to a desired position; inserting the capture wire through a lumen of an excision device and inserting the excision device into an inner cavity of the aspiration device and moving the excision device to a desired position; excising a lesion with the excision device; allowing the capture wire and the aspiration device to move relatively in a distal direction and a proximal direction at a frequency of 2 times/second to 5 times/second; and allowing the aspiration device to start aspiration of the object, or the excised lesion, captured by the capture unit. Accordingly, in the aspiration method, since the aspiration is started after the object captured by the capture unit effectively floats away from the capture unit, it is possible to prevent unnecessary aspiration of a body fluid while effectively aspirating the object captured by the capture unit with the aspiration device.

(9) In the aspiration method according to (7) or (8), the capture wire and the aspiration device may be relatively moved in the distal direction and the proximal direction at a frequency of less than 2 times/second in a state where a distal end opening that causes an aspiration force to act on outside of the aspiration device is surrounded by an object of interest. Accordingly, the aspiration method enables effective aspiration of a thrombus in the state where the distal end opening is surrounded by the object to be aspirated.

DETAILED DESCRIPTION

Figure 1:
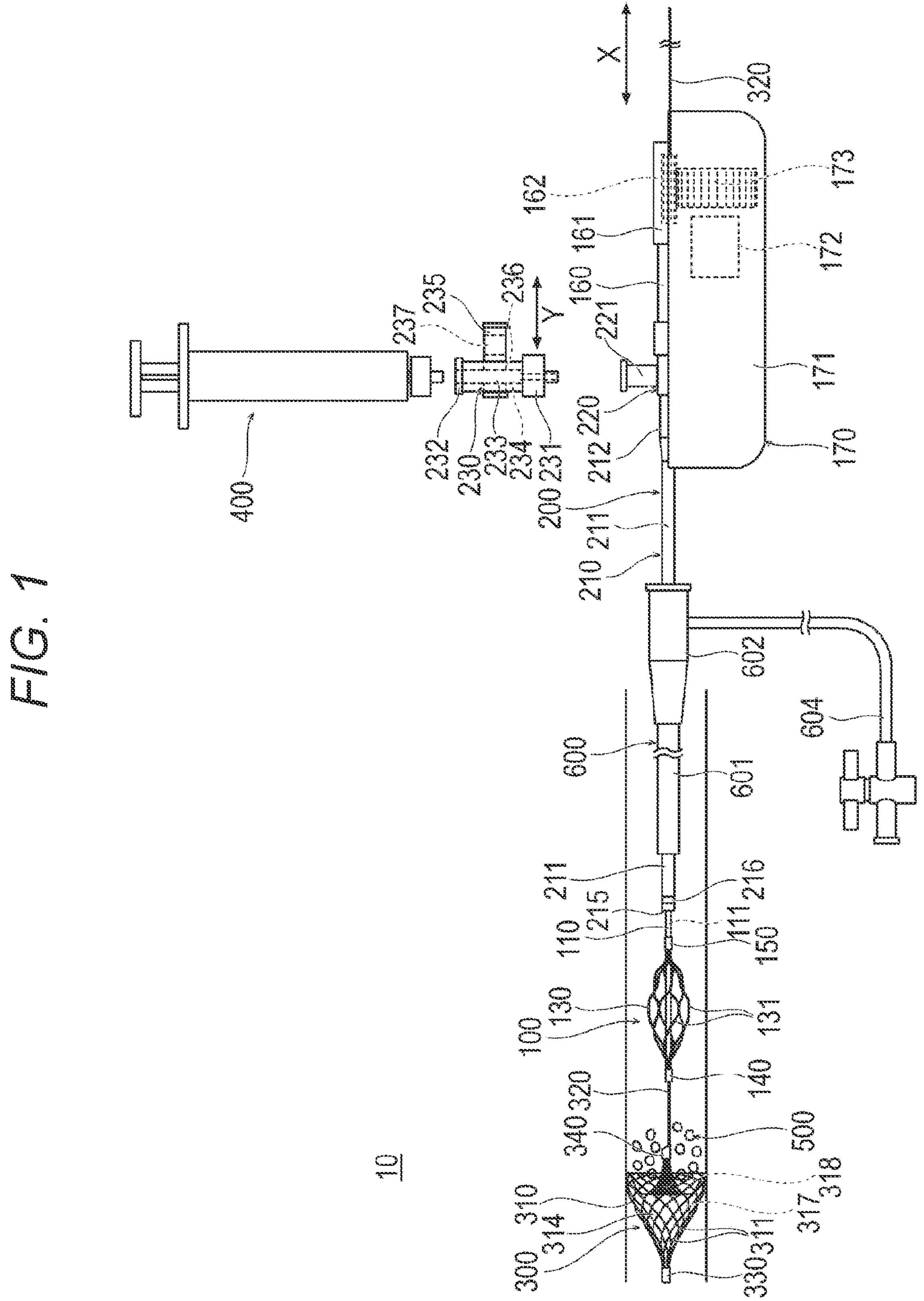
FIG. 1 is a plan view illustrating an aspiration system according an embodiment.

Set forth below with reference to the accompanying drawings is a detailed description of embodiments of an aspiration system and an aspiration method for capturing and aspirating an object flowing within a lumen of a living body. Note that dimensional ratios in the drawings may be exaggerated for illustration purpose and may differ from the actual dimensional ratios.

As illustrated in FIG. 1, an aspiration system 10 according to this embodiment includes an elongated excision device 100 that is inserted into a lumen of a living body such as a blood vessel (for example, vein) to excise an object such as a thrombus 500, an aspiration device 200 having the aspiration function, a capture device 300 including a capture unit 310 to be deployed in the lumen of the living body, a syringe 400, and an introducer sheath 600. Herein, a side of the excision device 100, aspiration device 200, capture device 300, and introducer sheath 600 to be inserted into the lumen of the living body is referred to as "the distal side", and a side to be operated is referred to as "the proximal side." In addition, a direction in which the excision device 100, aspiration device 200, and capture device 300 extend is referred to as the longitudinal direction X. Furthermore, herein, the source of a blood flow in a blood vessel is referred to as "the upstream side", and a direction of the blood flow is referred to as "the downstream side."

Note that the lumen of the living body where the aspiration system 10 is inserted is not limited to a blood vessel and may be, for example, a vascular channel, ureter, bile duct, oviduct, or hepatic duct. The object to be excised is not necessarily limited to the thrombus 500 and may be of any kind that may be present in the lumen of the living body such as plaque and calcified lesion.

First, the excision device 100 will be described. The excision device 100 according to this embodiment is inserted into a blood vessel to physically excise the thrombus 500. The term "excise" represents "to physically break an object by a structure" and does not limit the shape of the structure, the method of breaking, the extent of breaking, the range of breaking, or the shape of the broken object. The excision device 100 includes a drive shaft 110, an excision unit 130, a fixing portion 140, a sliding portion 150, a hub 160, and a drive unit 170.

The drive shaft 110 is an elongated tubular body that transmits torque to the excision unit 130. A proximal portion of the drive shaft 110 is rotatably placed in the hub 160. The drive shaft 110 has a lumen 111 that allows a capture wire 320 of the capture device 300 to be inserted through the lumen 111 of the drive shaft.

The drive shaft 110 has flexibility so as to move within a blood vessel. Furthermore, the drive shaft 110 preferably has high torsional rigidity to transmit torque to a distal portion from the proximal portion. The drive shaft 110 can be, for example, a metallic tubular body having a helical slit or a tubular body obtained by braiding a plurality of metallic wires into a tubular shape. An example of the material for the drive shaft 110 can include stainless steel.

The fixing portion 140 is a ring-shaped member that fixes the excision unit 130 to the drive shaft 110. The fixing portion 140 is fixed to the outer periphery of a distal end of the drive shaft 110. The fixing portion 140 is also fixed to a distal end of the excision unit 130.

The sliding portion 150 is a ring-shaped member that is slidable in the longitudinal direction X and placed closer to the proximal side than the fixing portion 140 on the outer periphery of the drive shaft 110. The sliding portion 150 is fixed to a proximal end of the excision unit 130.

The excision unit 130 is a member that expands within the blood vessel and rotates to excise an object such as the thrombus 500. The excision unit 130 is fixed to the distal portion of the drive shaft 110. The excision unit 130 can include a plurality of deformable wire rods 131 arranged in the circumferential direction. Each wire rod 131 desirably includes a material having shape memory behavior so as to deform elastically and largely (i.e., expands radially outward). A distal end of each wire rod 131 is fixed to the fixing portion 140. A proximal end of each wire rod 131 is fixed to the sliding portion 150. Substantially central portions of the wire rods 131 are curved and arranged in the circumferential direction at positions distant from the drive shaft 110 in the radially outward direction. With this configuration, the excision unit 130 bulges uniformly in the circumferential direction as a whole. In a natural state with no external force, the excision unit 130 expands radially. Along with the rotation of the drive shaft 110, the excision unit 130 rotates to excise the thrombus 500 within the blood vessel or stir the excised thrombus 500. The excision unit 130 contracts radially when being subject to a force that separates both ends in the longitudinal direction X. Alternatively, the excision unit 130 contracts radially when being subject to a force from the radially outer side to the inner side.

Note that the aspect of the excision unit 130 is not particularly limited. For example, instead of being formed by the plurality of wire rods 131, the excision unit 130 may be provided with abrasive grains or blades to fulfill the excision function. Furthermore, the excision unit 130 is not necessarily expandable or contractible.

The hub 160 is a member that is gripped and operated by an operator and is coupled to the drive unit 170. The hub 160 includes a hub body 161 where the proximal portion of the drive shaft 110 is placed and a driven gear 162 rotatably supported inside the hub body 161 and fixed to the drive shaft 110.

The hub body 161 rotatably houses the proximal portion of the drive shaft 110 and the driven gear 162. A part of the driven gear 162 is placed inside the hub body 161 and the other part is exposed to the outside of the hub body 161.

The drive unit 170 is a device to which the hub 160 is coupled and which supplies a drive force to the drive shaft 110. The drive unit 170 can include an enclosure 171 to which the hub 160 is coupled, a drive source 172 such as a motor that drives the drive shaft 110, and a drive gear 173 that is rotated by the drive source 172. The drive unit 170 can be of a portable type that is lifted and operated by the operator.

Next, the aspiration device 200 will be described. The aspiration device 200 can include an aspiration catheter 210, a Y-connector 220 coupled to a proximal portion of the aspiration catheter 210, and an opening-closing unit 230 serving as a stopcock coupled to the Y-connector 220.

The aspiration catheter 210 can include an elongated aspiration tube 211 and an aspiration hub 212 coupled to a proximal portion of the aspiration tube 211.

The aspiration tube 211 is a tubular body capable of aspirating the thrombus 500 and the like from a distal end opening 215. The aspiration tube 211 has flexibility, being capable of housing the drive shaft 110 rotatably and placed in the outer side of the drive shaft 110 in a coaxial manner. The aspiration tube 211 has a ring-shaped radiopaque contrast agent marker 216 at a predetermined position from a distal end toward the proximal side. The aspiration tube 211 may also be capable of contracting and housing the excision unit 130 of the excision device 100. The aspiration tube 211 has flexibility so as to move within the blood vessel. The aspiration tube 211 is fixed to the aspiration hub 212 on the proximal side.

The aspiration tube 211 is not particularly limited in outside diameter. For example, the outside diameter can range from 2.5 mm to 4.5 mm. The aspiration tube 211 is not particularly limited in inside diameter. For example, the inside diameter can range from 2.0 mm to 4.0 mm.

The Y-connector 220 includes an aspiration port 221 branching from an inner cavity that pierces the Y-connector 220 from a distal end to a proximal end. The Y-connector 220 causes an aspiration force supplied from the aspiration port 221 to act on the aspiration catheter 210. A distal portion of the Y-connector 220 is coupled to the aspiration hub 212 of the aspiration catheter 210. Note that the Y-connector 220 may be formed in an integrated manner with the aspiration hub 212. In other words, the aspiration port 221 may be formed in the aspiration hub 212. The aspiration hub 212 and the Y-connector 220 are gripped and operated by the operator and coupled to the drive unit 170.

Figure 4:
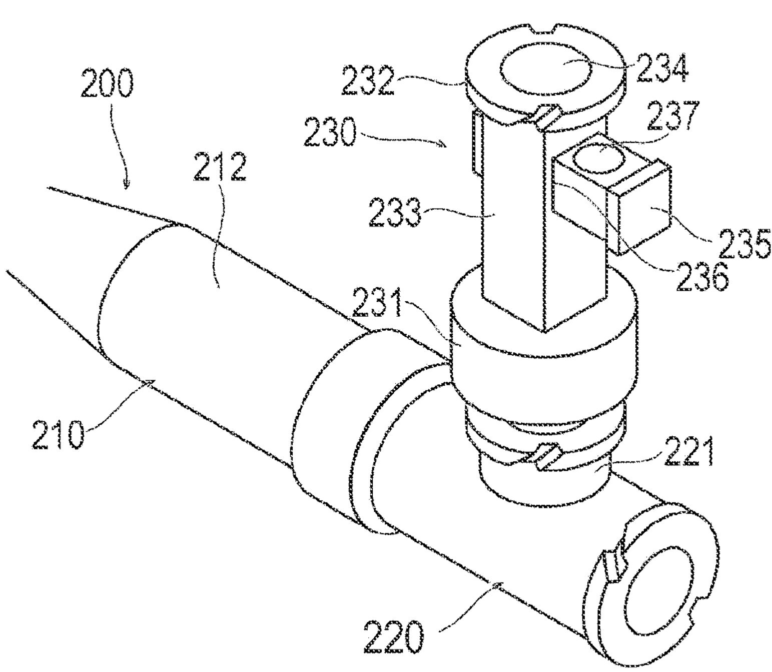
FIG. 4 is a perspective view illustrating a proximal portion of an aspiration device.

As illustrated in FIGS. 1, 4, and 5, the opening-closing unit 230 serving as a stopcock includes a first connection 231 connectable to the aspiration port 221, a second connection 232 to which the syringe 400 or the like is connectable, an opening-closing unit body 233 forming a passage 234 between the first connection 231 and the second connection 232, and an opening-closing operating portion 235 slidably coupled to the opening-closing unit body 233 in a linear opening-closing direction Y.

The first connection 231 is a male connector connectable to the aspiration port 221. The second connection 232 is a female connector to which the syringe 400 or the like is connectable.

The opening-closing unit body 233 is provided with a through-hole 236 that intersects the passage 234. The opening-closing operating portion 235 penetrates through the through-hole 236. The opening-closing operating portion 235 is slidably placed in the through-hole 236 of the opening-closing unit body 233. The opening-closing operating portion 235 is slidable in the linear opening-closing direction Y that intersects a direction in which the passage 234 extends. The opening-closing operating portion 235 is provided with a communication hole 237 extending in parallel with the passage 234.

Figure 5A:
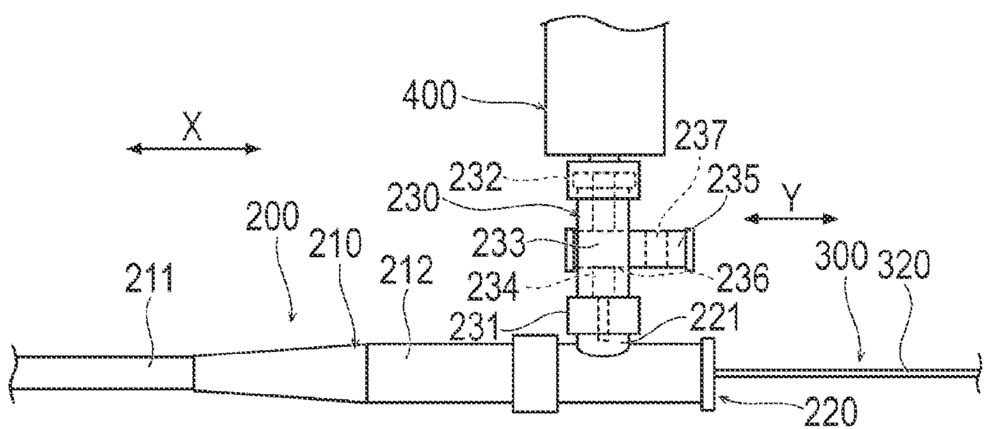
FIGS. 5A and 5B are plan views illustrating the aspiration device of the aspiration system and its surroundings, FIG. 5A illustrating a state where an opening-closing unit of the aspiration device is closed while FIG. 5B illustrating a state where the opening-closing unit of the aspiration device is opened.
Figure 5B:
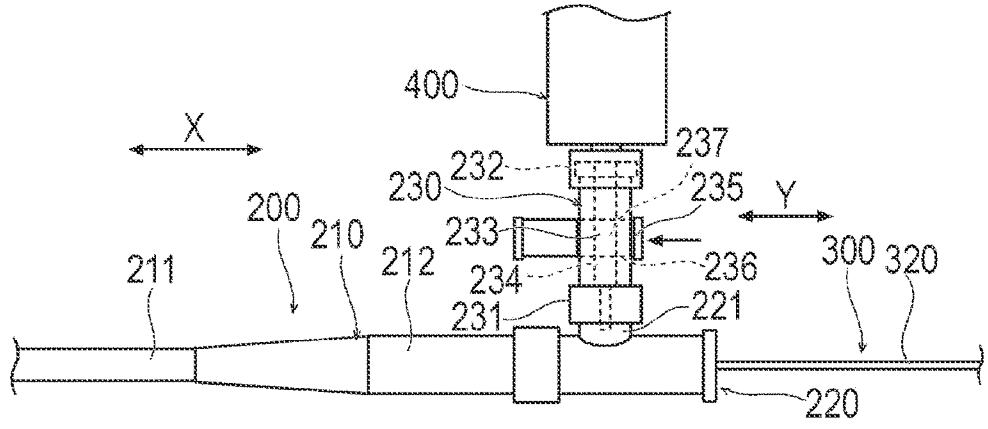

In an open state where the opening-closing unit body 233 is located at a first position in the opening-closing direction Y, as illustrated in FIG. 5B, the communication hole 237 is positioned in the passage 234. At this time, the passage 234 is opened between the first connection 231 and the second connection 232.

In a closed state where the opening-closing unit body 233 is located at a second position in the opening-closing direction Y, as illustrated in FIG. 5A, a portion of the opening-closing operating portion 235, different from the communication hole 237 (a portion with no hole), is positioned in the passage 234. At this time, the passage 234 is closed between the first connection 231 and the second connection 232 by the opening-closing operating portion 235.

The opening-closing unit 230 may be formed in an integrated manner with the Y-connector 220 and the aspiration hub 212.

Figure 2:
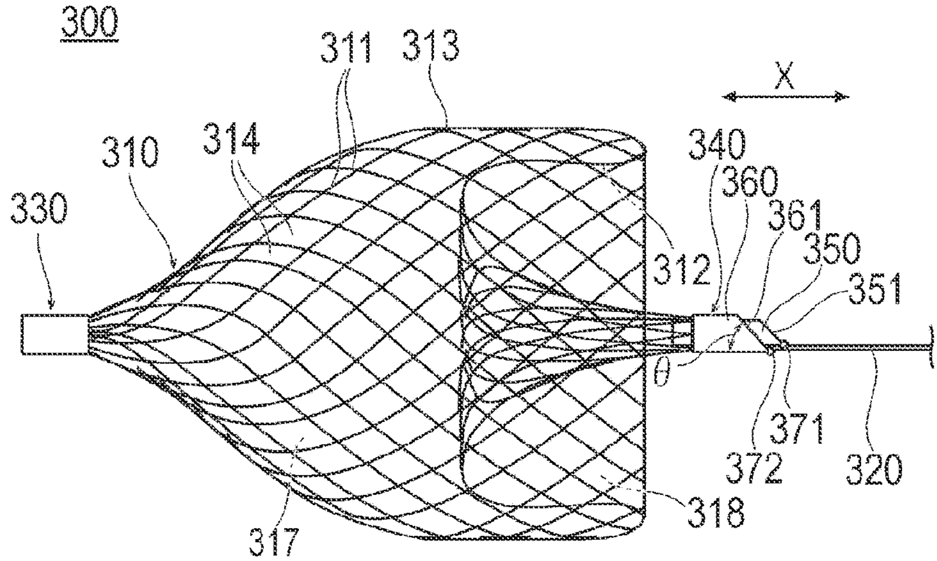
FIG. 2 is a plan view illustrating a distal portion of a capture device.
Figure 3:
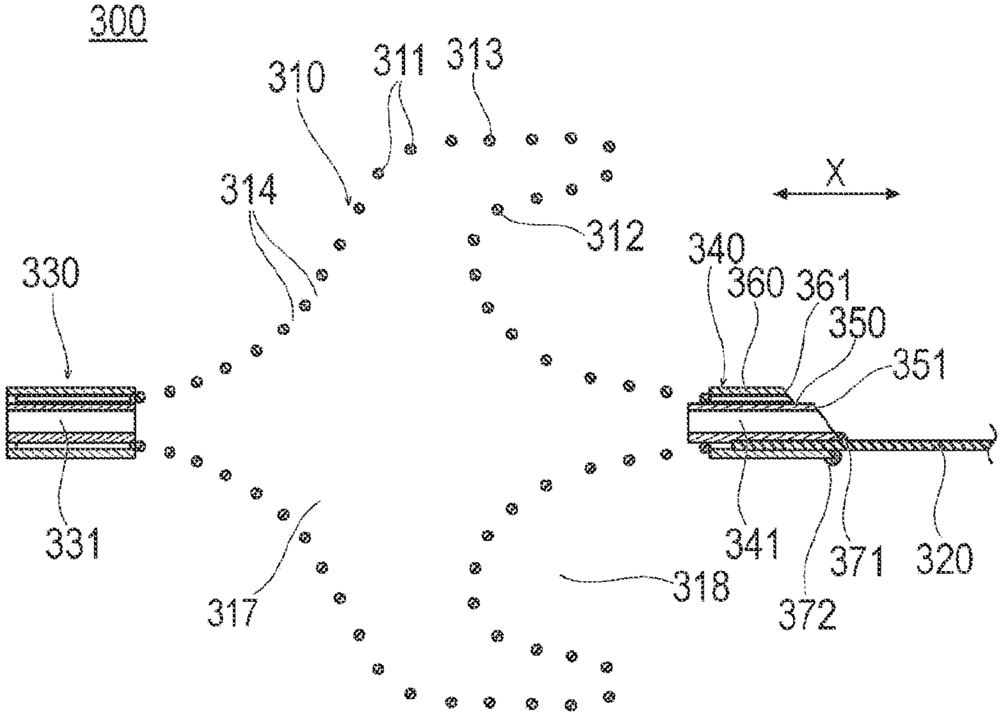
FIG. 3 is a cross-sectional view illustrating the distal portion of the capture device.

Next, the capture device 300 will be described. As illustrated in FIGS. 1 to 3, the capture device 300 has the capture unit 310 to be deployed in a lumen of a living body. In this embodiment, the capture unit 310 is shaped into a filter and is deployed in a blood vessel. The capture device 300 includes the capture unit 310 and the capture wire 320 extending from the capture unit 310 to the outside of the body. The capture wire 320 enables collection of the capture unit 310 deployed in the lumen of the living body and also functions as a guidewire that guides another device (for example, the excision device 100) to a desired position.

The capture unit 310 is a filter that captures an object such as the thrombus 500 that is excised by the excision device 100 and flows together with blood. The capture unit 310 includes a plurality of flexibly deformable linear members 311 braided into a net-like cylindrical body, a distal side coupler 330, and a proximal side coupler 340 coupled to the capture wire 320. An internal space 317 is formed inside the capture unit 310 that forms the cylindrical body. The plurality of linear members 311 can be braided with a gap 314 formed between the linear members 311.

The distal side coupler 330 clamps and fixes distal portions of the plurality of linear members 311 between two coaxially overlapping tubular bodies. The two tubular bodies and the plurality of linear members 311 are fixed with an adhesive. The distal side coupler 330 has a distal side through-hole 331 that pierces the distal side coupler 330 from a distal end to a proximal end. The distal side through-hole 331 may allow insertion of a guidewire. Note that the distal side through-hole 331 is not necessarily formed.

The proximal side coupler 340 clamps and fixes proximal portions of the plurality of linear members 311 and a distal portion of the capture wire 320 between an inner tube 350 and an outer tube 360 coaxially overlapping each other. The inner tube 350, the outer tube 360, the plurality of linear members 311, and the capture wire 320 can be fixed with an adhesive. The proximal side coupler 340 has a proximal side through-hole 341 that pierces the proximal side coupler 340 from a distal end to a proximal end. The proximal side through-hole 341 may allow insertion of a guidewire. A proximal end of the inner tube 350 has an inner tube bevel 351 inclined, for example, at an angle θ of more than 0 degrees and less than 90 degrees relative to the longitudinal direction X of the capture wire 320. A proximal end of the outer tube 360 has an outer tube bevel 361 inclined at an angle θ relative to the longitudinal direction X of the capture wire 320. The angle θ is not particularly limited and can be, for example, 5 degrees to 85 degrees. The inner tube bevel 351 and the outer tube bevel 361 are parallel to each other, and the inner tube bevel 351 is located closer to the proximal side than the outer tube bevel 361. In other words, a proximal portion of the inner tube 350 protrudes in the proximal direction from the proximal end of the outer tube 360 and is exposed to the outside. The most proximal portion of the inner tube bevel 351 and the most proximal portion of the outer tube bevel 361 are brought into line with the capture wire 320 in the circumferential direction of the proximal side coupler 340. Since the proximal portion of the inner tube 350 protrudes in the proximal direction from the proximal end of the outer tube 360, the proximal side coupler 340 smoothly enters through the distal end opening 215 of the aspiration tube 211. Furthermore, a distal end of the inner tube 350 protrudes toward the distal side from a distal end of the outer tube 360.

A part of the adhesive for bonding the inner tube 350, the outer tube 360, the plurality of linear members 311, and the capture wire 320 is exposed to the outside of the inner tube 350 and the outer tube 360. The adhesive has, as portions exposed to the outside, an inner tube protecting adhesive portion 371 that covers a portion of the inner tube 350 protruding most on the proximal side and an outer tube protecting adhesive portion 372 that covers a portion of the outer tube 360 protruding most on the proximal side. The inner tube protecting adhesive portion 371 and the outer tube protecting adhesive portion 372 can be formed of a resin material obtained by curing the adhesive. This configuration helps prevent disadvantages such as interference with the operation to put the thrombus 500 in the aspiration tube 211 and damage to the aspiration tube 211 which are caused when the protruding end of the inner tube 350 gets caught on the distal end opening 215 of the aspiration tube 211 of the aspiration device 200. The outer tube protecting adhesive portion 372 help prevent disadvantages such as interference with the operation to put the thrombus 500 in the aspiration tube 211 and damage to the aspiration tube 211 which are caused when the protruding end of the outer tube 360 gets caught on the distal end opening 215 of the aspiration tube 211 of the aspiration device 200.

In the natural state with no external force, the capture unit 310 is folded back in the longitudinal direction X by the linear members 311 due to their own elastic forces (restoring forces). When the capture unit 310 is folded back, the proximal side coupler 340 and the distal side coupler 330 approach each other. In the folded state, a first portion 312 of the plurality of linear members 311 coupled to the proximal side coupler 340 penetrates into a second portion 313 of the plurality of linear members 311 coupled to the distal side coupler 330. The first portion 312 of the linear members 311 coupled to the proximal side coupler 340 has a recessed shape opened toward the proximal side and forms a capture space 318 for capturing the thrombus 500 and the like.

The number of the linear members 311 is not particularly limited. The condition for braiding the linear members 311 is not particularly limited. The linear members 311 preferably include a material having ductility and examples of the material include shape memory alloys imparted with the shape memory effect or superelasticity by heat treatment, stainless steel, tantalum (Ta), titanium (Ti), platinum (Pt), gold (Au), tungsten (W), polyolefins such as polyethylene and polypropylene, polyamides, polyesters such as polyethylene terephthalate, fluorine-based polymers such as ethylene tetrafluoroethylene copolymer (ETFE), polyetheretherketone (PEEK), and polyimides.

The outer tube 360 is not particularly limited in outside diameter. For example, the outside diameter can range from 0.3 mm to 3.0 mm. The inner tube 350 is not particularly limited in inside diameter. For example, the inside diameter can range from 0.1 mm to 2.0 mm.

A maximum outside diameter of the capture unit 310 in an expanded state is appropriately selected depending on the inside diameter of the blood vessel where the capture unit 310 is to be applied. For example, the maximum outside diameter can range from 1 mm to 40 mm. An outside diameter of the capture unit 310 in a contracted state is appropriately selected depending on the inside diameter of the blood vessel where the capture unit 310 is to be applied. For example, the outside diameter can range from 0.3 mm to 4.0 mm. An axial length of the capture unit 310 in the expanded state is appropriately selected depending on the blood vessel where the capture unit 310 is to be applied. For example, the axial length can range from 20 mm to 150 mm.

The distal side coupler 330 and the proximal side coupler 340 are not particularly limited in material. For example, stainless steel and polyetheretherketone (PEEK) can be employed.

When the capture unit 310 is housed in the introducer sheath 600, the capture unit 310 deforms elastically and is brought into the contracted state with a small outside diameter. In the contracted state of the capture unit 310, the proximal side coupler 340 and the distal side coupler 330 separate from each other.

When the capture unit 310 is ejected from the introducer sheath 600, the capture unit 310 is deployed in the blood vessel in a nearly natural shape.

The introducer sheath 600 includes an elongated sheath 601, an introducer hub 602 coupled to a proximal portion of the sheath 601, and a port 604 branching from the introducer hub 602. The introducer sheath 600 is inserted percutaneously into the blood vessel to form an access route to the blood vessel. The sheath 601 is a tubular body inserted into the blood vessel to form an access route to the blood vessel. The sheath 601 has flexibility so as to move within the blood vessel.

With reference to a flowchart illustrated in FIG. 7, hereinafter described is a method of using the aspiration system 10 according to this embodiment as an example of aspirating and removing the thrombus 500 within a blood vessel.

First, an operator percutaneously inserts the introducer sheath 600 into a blood vessel on the upstream side (proximal side) of a lesion in the blood vessel and inserts the aspiration device 200 into the blood vessel through the introducer sheath 600 as illustrated in FIG. 1 (S10). A guidewire may be used to bring the aspiration device 200 to a desired position.

Next, the operator inserts the capture device 300 from the aspiration hub 212 of the aspiration device 200 into an inner cavity of the aspiration tube 211 and brings the capture device 300 to a desired position within the blood vessel. Note that the opening-closing operating portion 235 is in a closed state. Next, the operator causes the capture unit 310 of the capture device 300 to protrude from the distal end opening 215 of the aspiration tube 211. Accordingly, the distal side coupler 330 moves to approach the proximal side coupler 340. The capture unit 310 expands to an optimum size by its own restoring force and comes into contact with the inner wall surface of the blood vessel (S11). Due to its meshed shape, the capture unit 310 bites into the inner wall surface of the blood vessel and is firmly fixed. The maximum diameter of the expandable capture unit 310 used is larger than the diameter of the blood vessel where the capture unit 310 is inserted. For this reason, the capture unit 310 is not completely expanded within the blood vessel and generates an expansive force, thereby being fixed effectively to the wall of the blood vessel.

Note that the capture unit 310 is not necessarily folded back immediately after rejected from the aspiration tube 211 within the blood vessel. In this case, after the capture unit 310 is deployed in the blood vessel, the capture unit 310 is pushed toward the distal side by the capture wire 320, the aspiration tube 211, the excision device 100, and the like and folded back.

Next, the operator inserts an end of the capture wire 320 on the proximal side extending from the capture unit 310 to the outside of the body into the lumen 111 of the excision device 100 that is inserted into the aspiration device 200. Note that the excision unit 130 is contracted inside the aspiration tube 211. Next, the operator inserts the excision device 100 that is housed in the aspiration tube 211 with the contracted excision unit 130 into the blood vessel along the capture wire 320 and brings the excision device 100 to a desired position (near the lesion) within the blood vessel (S12). The capture wire 320 slides through the lumen 111 of the excision device 100. Next, the operator moves the aspiration tube 211 to the proximal side relative to the drive shaft 110 and ejects the excision unit 130 fixed to the proximal portion of the drive shaft 110 from the aspiration tube 211. When ejected from the aspiration tube 211, the excision unit 130 returns to its original shape by its own elastic force.

Next, the operator couples the hub 160 of the excision device 100 and the aspiration hub 212 to the drive unit 170. Accordingly, the drive gear 173 of the drive unit 170 meshes with the driven gear 162 of the excision device 100. With this configuration, rotating the drive source 172 causes the drive shaft 110 and the excision unit 130 to rotate.

Next, the operator actuates the drive source 172 to rotate the drive shaft 110 and the excision unit 130. The operator moves the drive unit 170 in the distal direction and the proximal direction alternately and excises the lesion by the excision unit 130 in the blood vessel (S13).

The thrombus 500 excised by the excision unit 130 reaches the capture unit 310 located on the downstream side. The blood passes through the gap 314 of the capture unit 310, and the filtered thrombus 500 is captured in the capture space 318. Under an environment with a blood flow, the thrombus 500 is subject to a force from the blood flow and sticks to the capture unit 310 without floating.

Upon completion of the excision of the thrombus 500 with the excision device 100, the operator stops the drive source 172 and stops the rotation of the drive shaft 110. Next, the operator unloads the hub 160 of the excision device 100 and the aspiration hub 212 of the aspiration device 200 from the drive unit 170. Subsequently, the operator moves the aspiration device 200 in the distal direction relative to the drive shaft 110 to house and contract the excision unit 130 in the aspiration tube 211. Next, the operator withdraws the excision device 100 to the outside of the body while leaving the aspiration device 200 in the blood vessel (S14).

Next, the operator places the aspiration device 200 in a desired position while checking the positions of the proximal side coupler 340 of the capture unit 310 and the contrast agent marker 216 of the aspiration device 200 in an X-ray fluoroscopic image. For example, a distal end of the contrast agent marker 216 of the aspiration device 200 is preferably at a distance L1 of about 7 mm to 10 mm toward the proximal side from the proximal end of the proximal side coupler 340 of the capture unit 310. At this time, the most distal position of the aspiration tube 211 is preferably at a distance L2 of about 12 mm to 15 mm toward the proximal side from the most distal position of the capture space 318. The aspiration tube 211 can have an outside diameter of, for example, 3.5 mm.

Next, as illustrated in FIG. 5A, while keeping the opening-closing operating portion 235 in the closed state, the operator connects the syringe 400 that has a pusher pushed into the second connection 232. The syringe 400 preferably has the function of fixing the pusher. Next, the operator pulls the pusher of the syringe 400 and fixes the syringe 400 with the pusher in a pulled state. Accordingly, the pressure inside the syringe 400 is held negative.

Next, in order to start the aspiration of the thrombus 500, the operator operates the opening-closing operating portion 235 to bring the opening-closing unit 230 in the open state as illustrated in FIG. 5B (S15). It is possible for the operator to bring the opening-closing unit 230 in the open state by simply moving the opening-closing operating portion 235 in the linear opening-closing direction Y. Since the operator holds both the capture wire 320 and the aspiration device 200 to operate those members separately, it may be difficult to perform a complicated operation. For example, in a two-way stopcock or a three-way stopcock typically used for medical use, the rotation of a cock enables switching between opening and closing. However, it may be difficult to operate the stopcock accurately with one hand and, for example, the rotation for the switching may be insufficient. In contrast, the opening-closing operating portion 235 enables switching between opening and closing relatively easily and reliably by being pushed in one direction with one hand, thereby reliably supplying an aspiration force to the aspiration tube 211.

When the opening-closing unit 230 is in the open state, an aspiration force of the syringe 400 acts on the aspiration tube 211 via the Y-connector 220 and the aspiration hub 212, and the thrombus 500 and blood are aspirated into the syringe 400 from the distal end opening 215 of the aspiration tube 211 through the aspiration tube 211 via the aspiration hub 212, the aspiration port 221, and the opening-closing unit 230.

Figure 6:
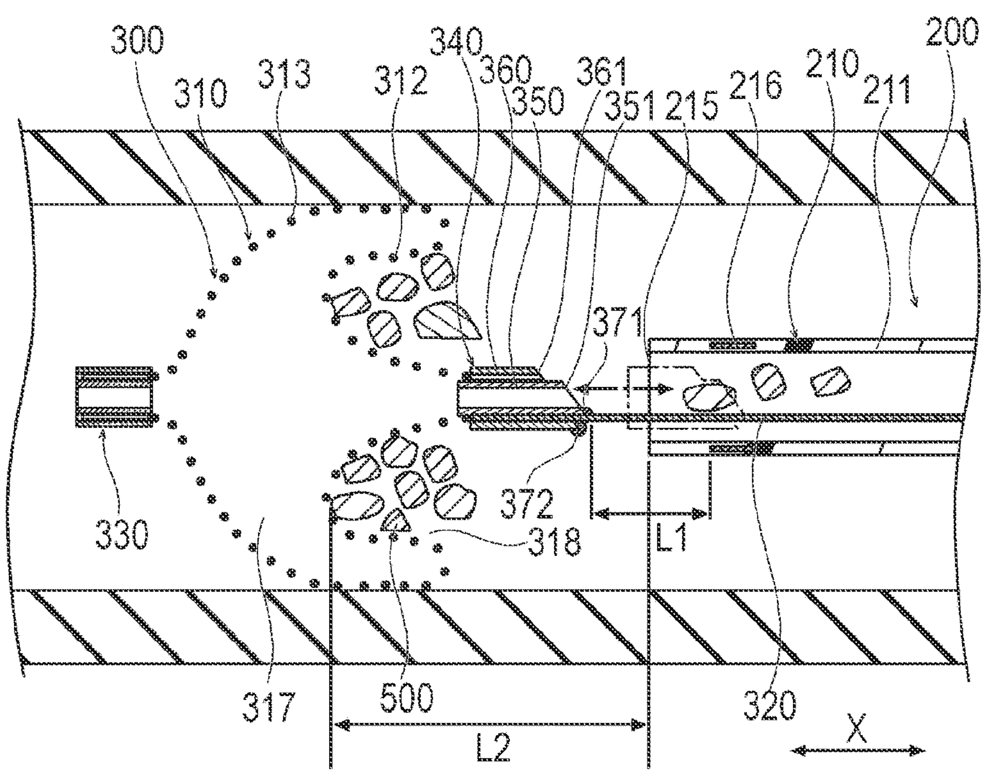
FIG. 6 is a cross-sectional view of the capture device and the aspiration device inserted into a blood vessel.

Next, as illustrated in FIG. 6, the operator causes the capture wire 320 to start reciprocating relative to the aspiration device 200 along the longitudinal direction X (S16). How to make the reciprocating motion is not limited as long as the proximal side coupler 340 and the distal end opening 215 move relative to one another. For this reason, the proximal side coupler 340 may be fixed and the distal end opening 215 may be moved axially. However, it is preferable that the proximal side coupler 340 moves or both the proximal side coupler 340 and the distal end opening 215 move so as to move the capture unit 310 by the reciprocating motion and cause the thrombus 500 to float.

When the capture wire 320 is reciprocated in the longitudinal direction X relative to the aspiration device 200, at least a part of the thrombus 500 captured in the capture space 318 of the capture unit 310 moves and floats away from the capture unit 310 toward the proximal side. Accordingly, the thrombus 500 separated from the capture unit 310 can be rather easily aspirated into the aspiration tube 211 from the distal end opening 215. Note that the position of the distal end opening 215 is fixed.

The frequency of the reciprocating motion can be, for example, preferably 2 times/second to 5 times/second, and more preferably, 3 times/second to 4 times/second. The reciprocating motion at too low a frequency slows down the moving speed of the capture unit 310 and stabilizes the position of the capture unit 310 but makes it difficult to move the thrombus 500 captured by the capture unit 310 because of the capture unit 310 moving too slow. In addition, during the reciprocating motion, the capture unit 310 is separated from the distal end opening 215 of the aspiration tube 211 for a relatively long time, which causes an increase in amount of blood removal.

The reciprocating motion at too high a frequency increases the moving speed of the capture unit 310 and easily moves the thrombus 500 captured by the capture unit 310 but may displace the capture unit 310 from the blood vessel because of the capture unit 310 moving too fast.

In contrast, the reciprocating motion at an appropriate frequency makes it possible to control the position of the capture unit 310, move the thrombus 500 captured by the capture unit 310, and reduce the amount of blood removal, thereby enhancing the aspiration probability (aspiration efficiency) of the thrombus 500.

When aspirating the thrombus 500, the thrombus 500 with a relatively small size moves in the proximal direction through the aspiration tube 211 from the distal end opening 215. On the other hand, the thrombus 500 with a relatively large size that is difficult to bring through the distal end opening 215 is adsorbed to the distal end opening 215 by an aspiration force and clogs the distal end opening 215. However, the proximal side coupler 340 enters through the distal end opening 215 when moving in the proximal direction during the reciprocating motion and protrudes in the distal direction from the distal end opening 215 when moving in the distal direction. Accordingly, every time the proximal side coupler 340 enters through the distal end opening 215, the thrombus 500 is pushed into the distal end opening 215 by the proximal side coupler 340. Therefore, even when the thrombus 500 is relatively large, the thrombus 500 is deformed or broken by the proximal side coupler 340 and the distal end opening 215 and is effectively aspirated into the aspiration tube 211 without clogging the distal end opening 215.

The operator repeats the reciprocating motion of the proximal side coupler 340 while applying negative pressure to the aspiration device 200 by the syringe 400, which enables the proximal side coupler 340 to repeat pushing the thrombus 500 into the aspiration tube 211. Accordingly, even when there is the thrombus 500 with a size that is difficult to collect in the aspiration tube 211 by an aspiration force, the thrombus 500 can be deformed or broken and effectively removed.

Since the proximal end of the proximal side coupler 340 is inclined, the proximal side coupler 340 smoothly enters through the distal end opening 215 of the aspiration tube 211. In addition, the portion of the inner tube 350 that protrudes most on the proximal side is covered with the inner tube protecting adhesive portion 371 and the portion of the outer tube 360 that protrudes most on the proximal side is covered with the outer tube protecting adhesive portion 372, thereby preventing the protruding portions from getting caught on the aspiration tube 211. Accordingly, it is possible to prevent disadvantages such as interference with the operation to put the thrombus 500 in the aspiration tube 211 and damage to the aspiration tube 211.

In addition, the proximal portion of the inner tube 350 of the proximal side coupler 340 is located closer to the proximal side than the proximal end of the outer tube 360, the inner tube 350 enters the aspiration tube 211 before the outer tube 360 enters the aspiration tube 211, thereby smoothing the next operation, that is, the outer tube 360 smoothly enters the aspiration tube 211. Accordingly, the proximal side coupler 340 smoothly enters through the distal end opening 215 of the aspiration tube 211, and the thrombus 500 is effectively broken and taken in the aspiration tube 211.

Incidentally, there is a case where many thrombi 500 are captured by the capture unit 310 and the distal end opening 215 of the aspiration device 200 is surrounded by the thrombi 500, for example, at the beginning of aspiration. Such a case does not necessarily require the reciprocating motion because the thrombi 500 can be rather easily aspirated without floating from the capture unit 310. For example, when the distal end opening 215 of the aspiration device 200 is surrounded by the thrombi 500 and buried in the thrombi 500, the frequency of the reciprocating motion is preferably, for example, less than 2 times/second. Accordingly, while effectively aspirating the thrombi 500, when a large thrombus 500 clogs the distal end opening 215, it is possible to deform or break the thrombus 500 with the proximal side coupler 340 and the distal end opening 215 and to aspirate the thrombus 500 into the aspiration tube 211. After eliminating the state where the distal end opening 215 of the aspiration device 200 is buried in the thrombi 500, the reciprocating motion at 2 times/second to 5 times/second enables effective aspiration of the thrombi 500.

In addition, the frequency of the reciprocating motion may be gradually increased or decreased.

Upon completion of the aspiration by the syringe 400, the operator brings the opening-closing operating portion 235 into the closed state. Note that the operator may keep the opening-closing operating portion 235 in the open state. Next, the operator pushes the aspiration device 200 in the distal direction while pulling the capture wire 320 in the proximal direction and houses the capture unit 310 in the aspiration tube 211, causing the aspiration tube 211 to contract. The operator, then, withdraws the aspiration device 200 and the capture device 300 from the blood vessel.

Figure 7:
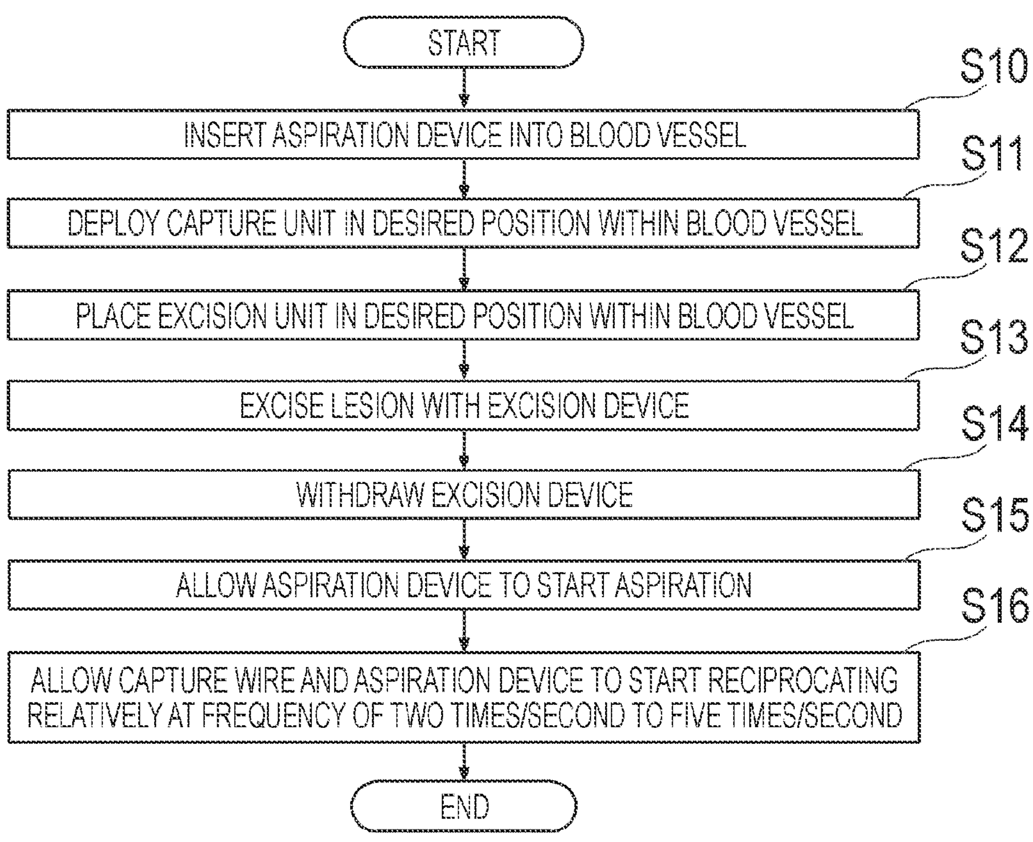
FIG. 7 is a flowchart illustrating a method of using the aspiration system.
Figure 8:
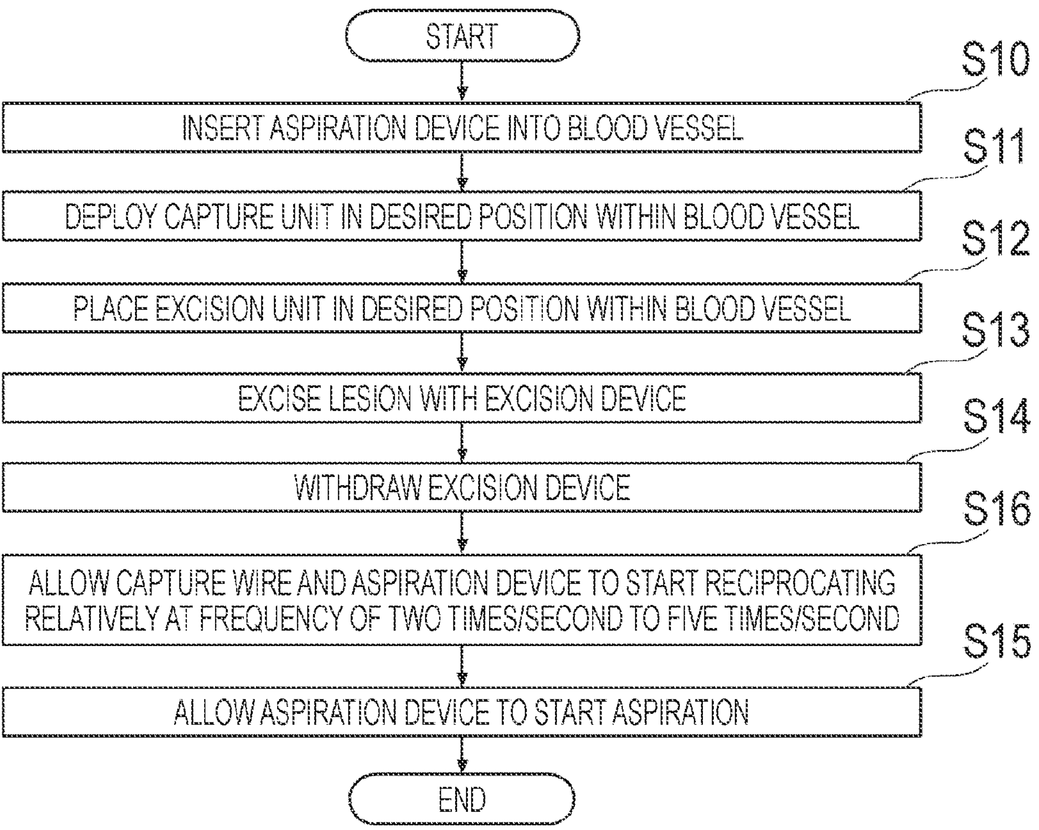
FIG. 8 is a flowchart illustrating another method of using the aspiration system.

In the above method, the relative reciprocating motion of the capture wire 320 and the aspiration device 200 is started (S16) after the aspiration by the aspiration device 200 is started (S15) as in the flowchart illustrated in FIG. 7. However, note that the aspiration by the aspiration device 200 may be started (S15) after the relative reciprocating motion of the capture wire 320 and the aspiration device 200 is started (S16) as in a modification illustrated in FIG. 8. In this case, after the relative reciprocating motion of the capture wire 320 and the aspiration device 200 is started and the thrombus 500 floats from the capture unit 310 and becomes rather easy to aspirate, the aspiration is started. This method helps prevent unnecessary blood removal and enables effective aspiration of the thrombus 500.

As described above, the aspiration system 10 according to this embodiment is capable of capturing and aspirating an object flowing within a lumen of a living body, and the aspiration system 10 includes the capture device 300 provided with the expandable capture unit 310 and the capture wire 320 extending from the capture unit 310, and the aspiration device 200 provided with the aspiration tube 211 having the distal end opening 215 and the aspiration port 221 communicating with an inner cavity of the aspiration tube 211. The capture unit 310 includes a plurality of linear members 311 that is deformable and braided into a net-like cylindrical body, the distal side coupler 330 that couples distal portions of the plurality of linear members 311, and the proximal side coupler 340 that couples proximal portions of the plurality of linear members 311 and is coupled to the capture wire 320. The proximal side coupler 340 includes the inner tube 350 and the outer tube 360 that surrounds the inner tube 350. The inner tube 350 has a proximal portion located closer to the proximal side than a proximal portion of the outer tube 360. With this configuration, in the aspiration system 10, the proximal portion of the inner tube 350 enters through the distal end opening 215 of the aspiration device 200 before the proximal portion of the outer tube 360 does, and subsequently, the proximal portion of the outer tube 360 is guided by the inner tube 350 and smoothly enters through the distal end opening 215. Accordingly, the proximal side coupler 340 of the capture unit 310 rather smoothly enters through the distal end opening 215 of the aspiration device 200. Therefore, the aspiration system 10 enables the object captured by the capture unit 310 to be drawn into the aspiration tube 211 more effectively by the proximal side coupler 340.

The inner tube 350 has the inner tube bevel 351 on the proximal side which is inclined at an angle of more than 0 degrees and less than 90 degrees relative to the longitudinal direction X of the capture wire 320. With this configuration, when the proximal side coupler 340 is drawn into the distal end opening 215 of the aspiration tube 211, it is possible to help prevent the most proximal ends of the inner tube 350 and the outer tube 360 protruding toward the proximal side from damaging the aspiration tube 211.

The outer tube 360 has the outer tube bevel 361 on the proximal side which is inclined at an angle of more than 0 degrees and less than 90 degrees relative to the longitudinal direction X of the capture wire 320. With this configuration, when the proximal side coupler 340 is drawn into the distal end opening 215 of the aspiration tube 211, it is possible to draw the outer tube 360 smoothly into the aspiration tube 211 along the outer tube bevel 361.

The most proximal end of the inner tube 350 protruding toward the proximal side and the most proximal end of the outer tube 360 protruding toward the proximal side are covered with a resin material. With this configuration, when the proximal side coupler 340 is drawn into the distal end opening 215 of the aspiration tube 211, it is possible to prevent the most proximal ends of the inner tube 350 and the outer tube 360 protruding toward the proximal side from damaging the aspiration tube 211.

The linear members 311 and the capture wire 320 can be clamped and fixed between the inner tube 350 and the outer tube 360. Accordingly, the linear members 311 and the capture wire 320 are clamped and firmly fixed between the outer tube 360 and the inner tube 350.

The aspiration device 200 includes the opening-closing unit 230 as a stopcock connectable to the aspiration port 221 and capable of opening and closing the passage 234. The opening-closing unit 230 includes the opening-closing operating portion 235 movable in the linear opening-closing direction. The passage 234 may be opened in the open state where the opening-closing operating portion 235 is located at the first position, and the passage 234 may be closed in the closed state where the opening-closing operating portion 235 is located at the second position different from the first position. Accordingly, the aspiration system 10 rather easily and reliably conducts starting and stopping operations for the aspiration by the aspiration device 200, thereby enhancing the operability.

An aspiration method according to this embodiment is a method for capturing and aspirating an object flowing within a lumen of a living body. The aspiration method involves: inserting the aspiration device 200 into the lumen of the living body; inserting the capture device 300 provided with the expandable capture unit 310 and the capture wire 320 extending from the capture unit 310 into an inner cavity of the aspiration device 200 and moving the capture device 300 to a desired position; inserting the capture wire 320 through the lumen 111 of the excision device 100 and inserting the excision device 100 into the inner cavity of the aspiration device 200 and moving the excision device 100 to a desired position; excising a lesion with the excision device 100; withdrawing the excision device 100 from the aspiration device 200; allowing the aspiration device 200 to start aspiration of the object, or the excised lesion, captured by the capture unit 310; and allowing the capture wire 320 and the aspiration device 200 to move relatively in the distal direction and the proximal direction at a frequency of 2 times/second to 5 times/second. Accordingly, in the aspiration method, since the object captured by the capture unit 310 effectively floats away from the capture unit 310, the object captured by the capture unit 310 is effectively aspirated by the aspiration device 200.

Another aspiration method according to this embodiment is a method for capturing and aspirating an object flowing within a lumen of a living body. The aspiration method involves: inserting the aspiration device 200 into the lumen of the living body; inserting the capture device 300 provided with the expandable capture unit 310 and the capture wire 320 extending from the capture unit 310 into an inner cavity of the aspiration device 200 and moving the capture device 300 to a desired position; inserting the capture wire 320 through the lumen 111 of the excision device 100 and inserting the excision device 100 into the inner cavity of the aspiration device 200 and moving the excision device 100 to a desired position; excising a lesion with the excision device 100; allowing the capture wire 320 and the aspiration device 200 to move relatively in the distal direction and the proximal direction at a frequency of 2 times/second to 5 times/second; and allowing the aspiration device 200 to start aspiration of the object, or the excised lesion, captured by the capture unit 310. Accordingly, in the aspiration method, since the aspiration is started after the object captured by the capture unit 310 effectively floats away from the capture unit 310, it is possible to prevent unnecessary aspiration (for example, blood removal) of a body fluid while effectively aspirating the object captured by the capture unit 310 with the aspiration device 200.

In the aspiration method, the capture wire 320 and the aspiration device 200 may be relatively moved in the distal direction and the proximal direction at a frequency of less than 2 times/second in a state where the distal end opening 215 that causes an aspiration force to act on the outside of the aspiration device 200 is surrounded by the object to be aspirated. Accordingly, the aspiration method enables effective aspiration of the thrombus 500 in a state where the distal end opening 215 is surrounded by the object to be aspirated. With the reciprocating motion at a frequency less than 2 times/second, the object captured by the capture unit 310 is less likely to float away from the capture unit 310, and the object remaining as a clot is brought close to or away from the distal end opening 215 and aspirated efficiently.

EXAMPLES

Figure 9:
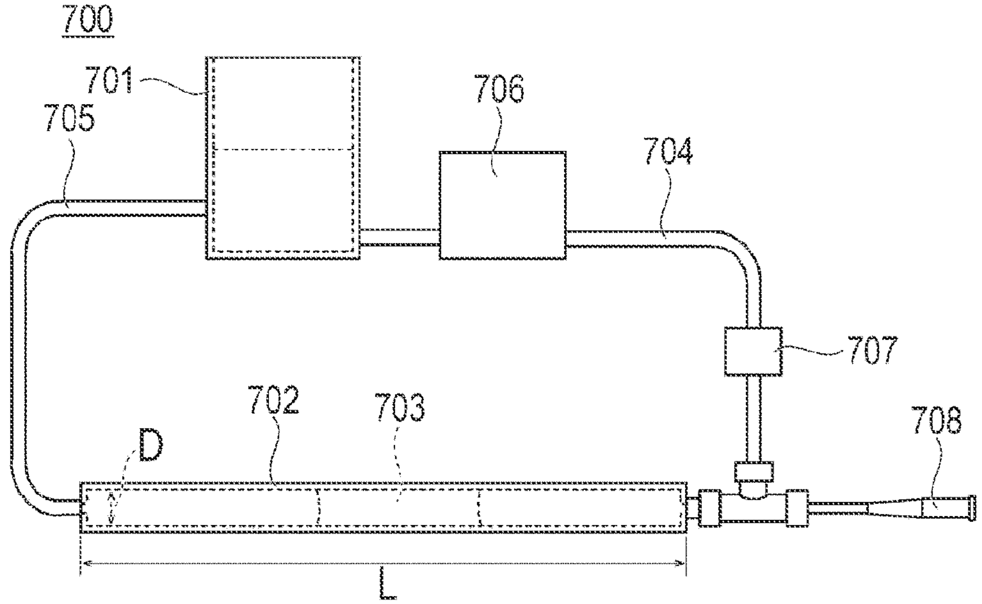
FIG. 9 is a schematic view illustrating a testing device.

A test was conducted to evaluate the level of aspiration of an object depending on the frequency of the reciprocating motion of the capture wire 320. As illustrated in FIG. 9, the test employed a testing device 700 having a tank 701 for storing saline as a liquid that simulates blood, a blood vessel model 702 that simulates a blood vessel, a thrombus model 703 that simulates a thrombus, a supply channel 704 for supplying the liquid from the tank 701 to the blood vessel model 702, a recovering channel 705 for returning the liquid from the blood vessel model 702 to the tank 701, a pump 706 placed in the supply channel 704 and used for pressurizing the liquid supplied from the tank 701, a flowmeter 707 placed in the supply channel 704 and used for detecting a flow rate of the liquid pressurized by the pump 706, and an introducer 708 connected between the flowmeter 707 of the supply channel 704 and the blood vessel model 702. The blood vessel model 702 was a transparent tube made of vinyl chloride having an inside diameter D of 19 mm and a length L of 109 mm. The thrombus model 703 was formed of gelatin as a material for clogging an inner cavity of the blood vessel model 702. The hardness (elastic modulus) of the thrombus model 703 was about 15 kPa. In the test, the pump 706 was activated in such a manner that a flow rate of the liquid detected by the flowmeter 707 was 1.2 L/second.

During the test, an examiner inserted the capture device 300 housing the capture unit 310 into the aspiration device 200 from the introducer 708. The maximum outside diameter of the expanded capture unit 310 was 32 mm, and the wire diameter (diameter) of the linear members 311 was 0.45 mm. The outside diameter of the proximal side coupler 340 of the capture unit 310 was 2.15 mm. The examiner allowed the aspiration tube 211 housing the capture device 300 to penetrate through the thrombus model 703 within the blood vessel model 702 and brought the aspiration tube 211 closer to the distal side than the blood vessel model 702. Next, the examiner allowed the capture unit 310 to protrude from the aspiration tube 211 and expand and brought the capture unit 310 into contact with the inner wall surface of the blood vessel model 702 in a folded state.

Figure 10:
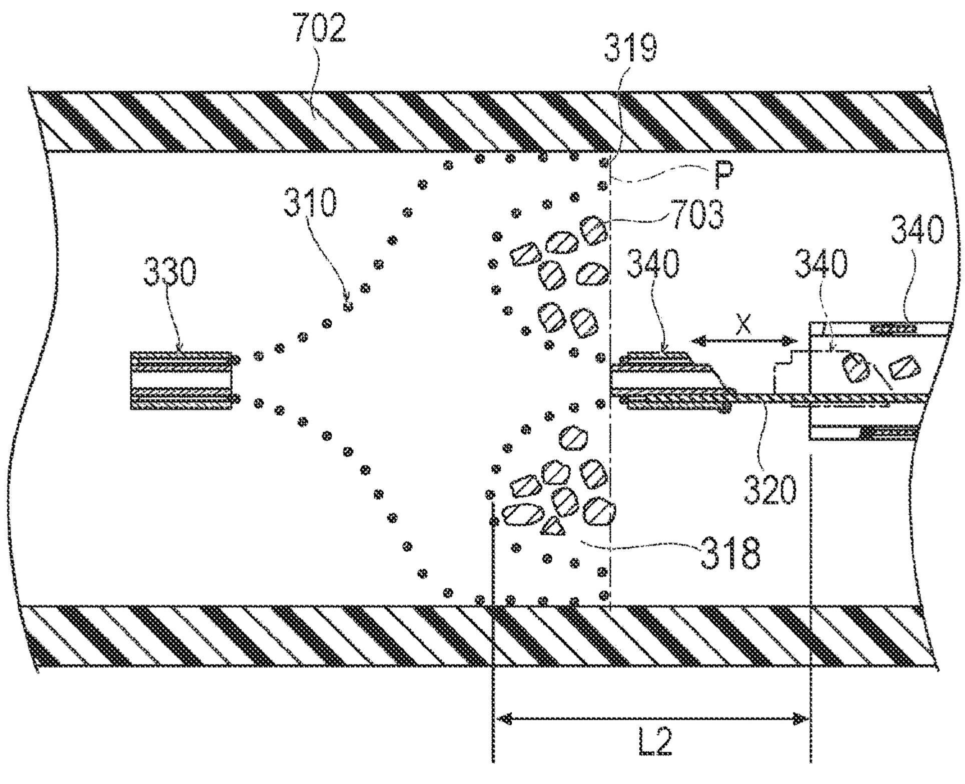
FIG. 10 is a schematic cross-sectional view illustrating an evaluation test by the testing device.

Next, the operator moved the distal end of the aspiration tube 211 closer to the proximal side than the thrombus model 703. Furthermore, the examiner allowed the excision unit 130 to contract so as to house the excision unit 130 in the aspiration tube 211, moved the excision unit 130 in the distal direction within the aspiration tube 211, allowed the excision unit 130 to protrude from the aspiration tube 211 and to expand within the inner cavity of the blood vessel model 702. After these steps, the operator connected the excision device 100 and the aspiration device 200 to the drive unit 170, and then, the examiner actuated the drive source 172 to rotate the excision unit 130 and moved the drive unit 170 alternately in the distal direction and the proximal direction, thereby excising the thrombus model 703 with the excision unit 130. The excised thrombus model 703 flowed due to a liquid flowing at a predetermined flow rate and was captured in the capture space 318 of the capture unit 310 as illustrated in FIG. 10. Next, the operator unloaded the aspiration device 200 from the drive unit 170 and withdrew the excision device 100, leaving the aspiration device 200.

Next, with regard to a position of a folded portion 319 of the folded capture unit 310 in the longitudinal direction X that was folded back and protruded toward the proximal side (reference position P), the operator brought the position into line with the distal end of the proximal side coupler 340. At this time, a distance L2 from the most distal position of the aspiration tube 211 to the most distal position of the capture space 318 was 13 mm. The aspiration tube 211 had an inside diameter of 2.64 mm.

Next, the operator repeated reciprocating motion at a constant frequency by moving the capture wire 320 in the proximal direction relative to the aspiration device 200, and then, in the distal direction to return the capture wire 320 to the reference position P. Furthermore, the examiner caused a negative pressure to act on the aspiration tube 211 by the syringe 400 connected to the aspiration device 200, thereby aspirating and removing the excised thrombus model 703 through the distal end opening 215 of the aspiration tube 211. The test was conducted in seven ways, increasing the frequency of the reciprocating motion by one from one time/second to seven times/second. In each test, the operator visually checked the behaviors of the capture unit 310 and the thrombus model 703 captured by the capture unit 310 and determined the amount of blood removal in the syringe 400.

The following Table 1 shows the test results.

TABLE 1

| Frequency of Reciprocating Motion Times/second | Test Results |
|---|---|
| 1 | The capture unit moved slowly, and the captured thrombus model was difficult to separate from the capture unit.<br>The amount of blood removal was large at the timing when the proximal side coupler was separated from the aspiration tube. |
| 2, 3, 4, 5 | Due to the motion of the capture unit, the captured thrombus model was easily separated from the capture unit.<br>The position of the capture unit relative to the blood vessel model was stable.<br>The amount of blood removal was small. |
| 6, 7 | The capture unit moved fast, and the captured thrombus model was easily separated from the capture unit.<br>The capture unit moved so fast that the position of the capture unit relative to the blood vessel model became unstable. |

Note that the present disclosure is not limited to the embodiment described above, and various modifications may be made by those skilled in the art within the technical idea of the present disclosure. For example, the opening-closing unit 230 that opens and closes the aspiration device 200 may switch between opening and closing by an operation in the linear opening-closing direction Y with another structure. For example, a rack, or a plate-like gear, may be placed in an opening-closing operating portion that moves in a linear manner, and a gear that meshes with the rack may be formed in a member provided with a communication hole. With this configuration, moving the opening-closing operating portion in a linear manner causes rotation of the member that includes the communication hole for opening and closing a passage and changes the direction of the communication hole, thereby switching between opening and closing of the passage. In addition, a cam mechanism (for example, cylindrical cam) may be utilized to convert linear motion into rotational motion.

The detailed description above describes to an aspiration system and an aspiration method for capturing and aspirating an object flowing within a lumen of a living body. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An aspiration method for capturing and aspirating an object flowing within a lumen of a living body, the aspiration method comprising:

inserting an aspiration device into the lumen of the living body;

inserting a capture device provided with an expandable capture unit and a capture wire extending from the capture unit into an inner cavity of the aspiration device and moving the capture device to a desired position;

inserting the capture wire through a lumen of an excision device and inserting the excision device into the inner cavity of the aspiration device and moving the excision device to a desired position;

excising a lesion with the excision device;

withdrawing the excision device from the aspiration device;

allowing the aspiration device to start aspiration of the object, or the excised lesion, captured by the capture unit; and allowing the capture wire and the aspiration device to move relatively in a distal direction and a proximal direction at a frequency of 2 times/second to 5 times/second.

2. The aspiration method according to claim 1, further comprising:

moving the capture wire and the aspiration device relatively in the distal direction and the proximal direction at a frequency of less than 2 times/second in a state where a distal end opening that causes an aspiration force to act on outside of the aspiration device is surrounded by the object to be aspirated.

3. The aspiration method according to claim 1, further comprising:

starting the aspiration of the object, or the excised lesion, captured by the capture unit before moving the capture wire and the aspiration device relatively in the distal direction and the proximal direction at the frequency of 2 times/second to 5 times/second.

4. The aspiration method according to claim 1, further comprising:

starting the moving of the capture wire and the aspiration device relatively in the distal direction and the proximal direction at the frequency of 2 times/second to 5 times/second before the aspiration of the object, or the excised lesion, captured by the capture unit.

5. The aspiration method according to claim 1, wherein the capture unit includes a plurality of linear members that is deformable and braided into a net-like cylindrical body, a distal side coupler that couples distal portions of the plurality of linear members, and a proximal side coupler that couples proximal portions of the plurality of linear members and is coupled to the capture wire, the proximal side coupler includes an inner tube and an outer tube that surrounds the inner tube, and the inner tube has a proximal portion located closer to a proximal side of the proximal side coupler than a proximal portion of the outer tube.

6. An aspiration method for capturing and aspirating an object flowing within a lumen of a living body, the aspiration method comprising:

inserting an aspiration device into the lumen of the living body;

inserting a capture device provided with an expandable capture unit and a capture wire extending from the capture unit into an inner cavity of the aspiration device and moving the capture device to a desired position;

inserting the capture wire through a lumen of an excision device and inserting the excision device into the inner cavity of the aspiration device and moving the excision device to a desired position;

excising a lesion with the excision device;

allowing the capture wire and the aspiration device to move relatively in a distal direction and a proximal direction at a frequency of 2 times/second to 5 times/second; and allowing the aspiration device to start aspiration of the object, or the excised lesion, captured by the capture unit.

7. The aspiration method according to claim 6, wherein the capture wire and the aspiration device are relatively moved in the distal direction and the proximal direction at a frequency of less than 2 times/second in a state where a distal end opening that causes an aspiration force to act on outside of the aspiration device is surrounded by the object to be aspirated.

8. The aspiration method according to claim 6, further comprising:

starting the aspiration of the object, or the excised lesion, captured by the capture unit before moving the capture wire and the aspiration device relatively in the distal direction and the proximal direction at the frequency of 2 times/second to 5 times/second.

9. The aspiration method according to claim 6, further comprising:

starting the moving of the capture wire and the aspiration device relatively in the distal direction and the proximal direction at the frequency of 2 times/second to 5 times/second before the aspiration of the object, or the excised lesion, captured by the capture unit.

10. The aspiration method according to claim 6, wherein the capture unit includes a plurality of linear members that is deformable and braided into a net-like cylindrical body, a distal side coupler that couples distal portions of the plurality of linear members, and a proximal side coupler that couples proximal portions of the plurality of linear members and is coupled to the capture wire, the proximal side coupler includes an inner tube and an outer tube that surrounds the inner tube; and the inner tube has a proximal portion located closer to a proximal side of the proximal side coupler than a proximal portion of the outer tube.

* * * * *